(12) United States Patent
Fertig et al.

(10) Patent No.: US 8,785,153 B2
(45) Date of Patent: Jul. 22, 2014

(54) ANTIBODIES AGAINST HUMAN IL33R AND USES THEREOF

(75) Inventors: Georg Fertig, Penzberg (DE); Jens Fischer, Weilheim (DE); Guy Georges, Habach (DE); Klaus Kaluza, Weilheim (DE); Valeria Lifke, Penzberg (DE); Joerg Moelleken, Munich (DE); Sonja Offner, Penzberg (DE); Achal Pashine, Mahwah, NJ (US); Stefan Seeber, Penzberg (DE)

(73) Assignee: Hoffmann-La Roche, Inc., Litle Falls, NJ (US)

( * ) Notice: Subject to any disclaimer, the term of this patent is extended or adjusted under 35 U.S.C. 154(b) by 152 days.

(21) Appl. No.: 13/402,399

(22) Filed: Feb. 22, 2012

(65) Prior Publication Data

US 2012/0213774 A1 Aug. 23, 2012

(30) Foreign Application Priority Data

Feb. 23, 2011 (EP) ..................................... 11155684

(51) Int. Cl.
*C12P 21/08* (2006.01)

(52) U.S. Cl.
USPC .... 435/69.1; 530/350; 530/387.1; 530/387.3; 530/388.22; 536/23.5; 435/320.1; 435/325

(58) Field of Classification Search
USPC ....................... 530/350, 387.1, 387.3, 388.22; 435/69.1, 320.1, 325; 536/23.5
See application file for complete search history.

(56) References Cited

PUBLICATIONS

Palmer et al., "Inhibition of Interleukin-33 Signaling Attenuates the Severity of Experimental Arthritis" Arthritis & Rheumatism 60(3):738-749 (Mar. 2009).
Seidelin et al., "IL-33 is upregulated in colonocytes of ulcerative colitis" Immunology Letters 128:80-85 ( 2010).

*Primary Examiner* — Stephen Rawlings
(74) *Attorney, Agent, or Firm* — Bonny G. Yeung

(57) ABSTRACT

An antibody binding to IL33R characterized in that the heavy chain variable domain comprises a CDR3 region of SEQ ID NO:1, a CDR2 region of SEQ ID NO:2 and a CDR1 region of SEQ ID NO:3 and in that the light chain variable domain comprises a CDR3 region of SEQ ID NO:4, a CDR2 region of SEQ ID NO:5 and a CDR1 region of SEQ ID NO:6 or a chimeric, humanized or T cell epitope depleted antibody variant thereof has advantageous properties for the treatment of inflammatory diseases.

16 Claims, No Drawings

SEQUENCE LISTING

```
<160> NUMBER OF SEQ ID NOS: 34

<210> SEQ ID NO 1
<211> LENGTH: 13
<212> TYPE: PRT
<213> ORGANISM: Oryctolagus cuniculus

<400> SEQUENCE: 1

Asp Gln Tyr Arg Ser Ser Gly Val Ser Asp Tyr Asp Ile
1               5                   10

<210> SEQ ID NO 2
<211> LENGTH: 16
<212> TYPE: PRT
<213> ORGANISM: Oryctolagus cuniculus

<400> SEQUENCE: 2

Tyr Ile Trp Ser Asp Asp Asn Thr Tyr Tyr Ala Ser Trp Ala Lys Gly
1               5                   10                  15

<210> SEQ ID NO 3
<211> LENGTH: 5
<212> TYPE: PRT
<213> ORGANISM: Oryctolagus cuniculus

<400> SEQUENCE: 3

Ser His Asp Met Ser
1               5

<210> SEQ ID NO 4
<211> LENGTH: 11
<212> TYPE: PRT
<213> ORGANISM: Oryctolagus cuniculus

<400> SEQUENCE: 4

Leu Gly Gly Tyr Asp Asp Asp Ala Asp Asn Thr
1               5                   10

<210> SEQ ID NO 5
<211> LENGTH: 7
<212> TYPE: PRT
<213> ORGANISM: Oryctolagus cuniculus

<400> SEQUENCE: 5

Lys Ala Ser Thr Leu Ala Ser
1               5
```

<210> SEQ ID NO 6
<211> LENGTH: 13
<212> TYPE: PRT
<213> ORGANISM: Oryctolagus cuniculus

<400> SEQUENCE: 6

Gln Ser Ser Gln Ser Val Gly Asn Asn Asn Asp Leu Ala
1               5                   10

<210> SEQ ID NO 7
<211> LENGTH: 118
<212> TYPE: PRT
<213> ORGANISM: Oryctolagus cuniculus

<400> SEQUENCE: 7

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser His Asp
            20                  25                  30

Met Ser Trp Val Arg Gln Ala Pro Gly Lys Gly Leu Glu Trp Ile Gly
        35                  40                  45

Tyr Ile Trp Ser Asp Asp Asn Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Asp Gln
                85                  90                  95

Tyr Arg Ser Ser Gly Val Ser Asp Tyr Asp Ile Trp Gly Pro Gly Thr
            100                 105                 110

Leu Val Thr Val Ser Ser
            115

<210> SEQ ID NO 8
<211> LENGTH: 111
<212> TYPE: PRT
<213> ORGANISM: Oryctolagus cuniculus

<400> SEQUENCE: 8

Ala Ala Val Leu Thr Gln Thr Pro Ser Pro Val Ser Ala Ala Val Gly
1               5                   10                  15

Gly Thr Val Thr Ile Ser Cys Gln Ser Ser Gln Ser Val Gly Asn Asn
            20                  25                  30

Asn Asp Leu Ala Trp Tyr Gln Gln Lys Pro Gly Gln Pro Pro Lys Ile
        35                  40                  45

Leu Ile Tyr Lys Ala Ser Thr Leu Ala Ser Gly Val Pro Ser Arg Phe
    50                  55                  60

Glu Gly Ser Gly Ser Gly Thr Gln Phe Thr Leu Thr Ile Ser Asp Val
65                  70                  75                  80

Gln Cys Asp Asp Ala Ala Thr Tyr Tyr Cys Leu Gly Gly Tyr Asp Asp
                85                  90                  95

Asp Ala Asp Asn Thr Phe Gly Gly Gly Thr Glu Val Val Val Lys
            100                 105                 110

<210> SEQ ID NO 9
<211> LENGTH: 330
<212> TYPE: PRT
<213> ORGANISM: homo sapiens

<400> SEQUENCE: 9

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 10
<211> LENGTH: 330
<212> TYPE: PRT
<213> ORGANISM: homo sapiens

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

```
Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
             100                 105                 110

Pro Ala Pro Glu Leu Leu Gly Gly Pro Ser Val Phe Leu Phe Pro Pro
         115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 11
<211> LENGTH: 330
<212> TYPE: PRT
<213> ORGANISM: homo sapiens

<400> SEQUENCE: 11

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80
```

```
Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 12
<211> LENGTH: 107
<212> TYPE: PRT
<213> ORGANISM: homo sapiens

<400> SEQUENCE: 12

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

```
<210> SEQ ID NO 13
<211> LENGTH: 9
<212> TYPE: PRT
<213> ORGANISM: Artificial
<220> FEATURE:
<223> OTHER INFORMATION: Replaced ST2 sequence fragment 1 for mut1

<400> SEQUENCE: 13

Asp Tyr Leu Met Tyr Ser Thr Val Ser
1               5

<210> SEQ ID NO 14
<211> LENGTH: 8
<212> TYPE: PRT
<213> ORGANISM: Artificial
<220> FEATURE:
<223> OTHER INFORMATION: Replaced ST2 sequence fragment 2 for mut1

<400> SEQUENCE: 14

Ser Glu Lys Asn Ser Lys Ile Tyr
1               5

<210> SEQ ID NO 15
<211> LENGTH: 8
<212> TYPE: PRT
<213> ORGANISM: Artificial
<220> FEATURE:
<223> OTHER INFORMATION: Replaced ST2 sequence fragment 3 for mut1

<400> SEQUENCE: 15

Arg Ala His Lys Ser Phe Leu Val
1               5

<210> SEQ ID NO 16
<211> LENGTH: 8
<212> TYPE: PRT
<213> ORGANISM: Artificial
<220> FEATURE:
<223> OTHER INFORMATION: Replaced ST2 sequence fragment 4 for mut1

<400> SEQUENCE: 16

Leu Ala Ala Val Leu Trp Gln Leu
1               5

<210> SEQ ID NO 17
<211> LENGTH: 9
<212> TYPE: PRT
<213> ORGANISM: Artificial
<220> FEATURE:
<223> OTHER INFORMATION: IL-1R fragment 1 mut1, replacing ST2 fragment
      SEQ13

<400> SEQUENCE: 17

Ala Gln Ala Ile Phe Lys Gln Lys Leu
1               5

<210> SEQ ID NO 18
<211> LENGTH: 8
<212> TYPE: PRT
<213> ORGANISM: Artificial
<220> FEATURE:
<223> OTHER INFORMATION: IL-1R fragment 2 mut2, replacing ST2 fragment
      SEQ14

<400> SEQUENCE: 18

Val Ala Gly Asp Gly Gly Leu Val
1               5
```

<210> SEQ ID NO 19
<211> LENGTH: 8
<212> TYPE: PRT
<213> ORGANISM: Artificial
<220> FEATURE:
<223> OTHER INFORMATION: IL-1R fragment 3 mut3, replacing ST2 fragment
      SEQ15

<400> SEQUENCE: 19

Ser Gly Val Lys Asp Arg Leu Ile
1               5

<210> SEQ ID NO 20
<211> LENGTH: 8
<212> TYPE: PRT
<213> ORGANISM: Artificial
<220> FEATURE:
<223> OTHER INFORMATION: IL-1R fragment 4 mut4, replacing ST2 fragment SEQ16

<400> SEQUENCE: 20

Ser Asp Ile Ala Tyr Trp Lys Trp
1 5

<210> SEQ ID NO 21
<211> LENGTH: 120
<212> TYPE: PRT
<213> ORGANISM: Artificial
<220> FEATURE:
<223> OTHER INFORMATION: heavy chain variable domain, humanized ra170 11.12(VH11)

<400> SEQUENCE: 21

Val Gln Leu Val Gln Ser Gly Ala Glu Val Lys Lys Pro Gly Ala Ser
1 5 10 15

Val Lys Val Ser Cys Lys Ala Ser Gly Phe Ser Leu Ser Ser His Asp
20 25 30

Ile Ser Trp Val Arg Gln Ala Pro Gly Gln Gly Leu Glu Trp Met Gly
35 40 45

Tyr Ile Trp Ser Asp Glu Ser Thr Tyr Tyr Ala Ser Trp Ala Gln Gly
50 55 60

Arg Val Thr Met Thr Thr Asp Thr Ser Thr Ser Thr Ala Tyr Met Glu
65 70 75 80

Leu Arg Ser Leu Arg Ser Asp Asp Thr Ala Val Tyr Tyr Cys Ala Arg
85 90 95

Asp Gln Tyr Arg Ser Ser Gly Val Ser Asp Tyr Asp Ile Trp Gly Pro
100 105 110

Gly Thr Leu Val Thr Val Ser Ser
115 120

<210> SEQ ID NO 22
<211> LENGTH: 5
<212> TYPE: PRT
<213> ORGANISM: Artificial
<220> FEATURE:
<223> OTHER INFORMATION: heavy chain CDR1, Mab ra170 11.12

<400> SEQUENCE: 22

Ser His Asp Ile Ser
1 5

<210> SEQ ID NO 23
<211> LENGTH: 16

```
<212> TYPE: PRT
<213> ORGANISM: Artificial
<220> FEATURE:
<223> OTHER INFORMATION: heavy chain CDR2, Mab ra170 11.12

<400> SEQUENCE: 23

Tyr Ile Trp Ser Asp Glu Ser Thr Tyr Tyr Ala Ser Trp Ala Gln Gly
1               5                   10                  15

<210> SEQ ID NO 24
<211> LENGTH: 13
<212> TYPE: PRT
<213> ORGANISM: Artificial
<220> FEATURE:
<223> OTHER INFORMATION: heavy chain CDR3, Mab ra170 11.12

<400> SEQUENCE: 24

Asp Gln Tyr Arg Ser Ser Gly Val Ser Asp Tyr Asp Ile
1               5                   10

<210> SEQ ID NO 25
<211> LENGTH: 120
<212> TYPE: PRT
<213> ORGANISM: Artificial
<220> FEATURE:
<223> OTHER INFORMATION: heavy chain variable domain, humanized ra170
      10.12(VH10)

<400> SEQUENCE: 25

Val Gln Leu Val Gln Ser Gly Ala Glu Val Lys Lys Pro Gly Ala Ser
1               5                   10                  15

Val Lys Val Ser Cys Lys Ala Ser Gly Phe Ser Leu Ser Ser His Asp
            20                  25                  30

Ile Ser Trp Val Arg Gln Ala Pro Gly Gln Gly Leu Glu Trp Met Gly
        35                  40                  45

Tyr Ile Trp Ser Asp Glu Asn Thr Tyr Tyr Ala Ser Trp Ala Gln Gly
    50                  55                  60

Arg Val Thr Met Thr Thr Asp Thr Ser Thr Ser Thr Ala Tyr Met Glu
65                  70                  75                  80

Leu Arg Ser Leu Arg Ser Asp Asp Thr Ala Val Tyr Tyr Cys Ala Arg
                85                  90                  95

Asp Gln Tyr Arg Ser Ser Gly Val Ser Asp Tyr Asp Ile Trp Gly Pro
            100                 105                 110

Gly Thr Leu Val Thr Val Ser Ser
        115                 120

<210> SEQ ID NO 26
<211> LENGTH: 5
<212> TYPE: PRT
<213> ORGANISM: Artificial
<220> FEATURE:
<223> OTHER INFORMATION: heavy chain CDR1, Mab ra170 10.12

<400> SEQUENCE: 26

Ser His Asp Ile Ser
1               5

<210> SEQ ID NO 27
<211> LENGTH: 16
<212> TYPE: PRT
<213> ORGANISM: Artificial
<220> FEATURE:
<223> OTHER INFORMATION: heavy chain CDR2, Mab ra170 10.12
```

<400> SEQUENCE: 27

Tyr Ile Trp Ser Asp Glu Asn Thr Tyr Tyr Ala Ser Trp Ala Gln Gly
1               5                   10                  15

<210> SEQ ID NO 28
<211> LENGTH: 13
<212> TYPE: PRT
<213> ORGANISM: Artificial
<220> FEATURE:
<223> OTHER INFORMATION: heavy chain CDR3, Mab ra170 10.12

<400> SEQUENCE: 28

Asp Gln Tyr Arg Ser Ser Gly Val Ser Asp Tyr Asp Ile
1               5                   10

<210> SEQ ID NO 29
<211> LENGTH: 327
<212> TYPE: PRT
<213> ORGANISM: homo sapiens

<400> SEQUENCE: 29

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

-continued

```
Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 30
<211> LENGTH: 111
<212> TYPE: PRT
<213> ORGANISM: Artificial
<220> FEATURE:
<223> OTHER INFORMATION: light chain variable domain, humanized ra170
      (11.12 and 10.12)

<400> SEQUENCE: 30

Ala Ala Val Met Thr Gln Ser Pro Ala Thr Leu Ser Val Ser Pro Gly
1               5                   10                  15

Glu Arg Ala Thr Leu Ser Cys Arg Ser Ser Gln Ser Val Gly Asn Asn
            20                  25                  30

Asn Asp Leu Ala Trp Tyr Gln Gln Lys Pro Gly Gln Ala Pro Arg Leu
        35                  40                  45

Leu Ile Tyr Lys Ala Ser Thr Arg Ala Thr Gly Ile Pro Ala Arg Phe
    50                  55                  60

Ser Gly Ser Gly Ser Gly Thr Glu Phe Thr Leu Thr Ile Ser Ser Leu
65                  70                  75                  80

Gln Ser Glu Asp Phe Ala Val Tyr Tyr Cys Leu Gly Gly Tyr Asp Asp
                85                  90                  95

Asp Ala Asp Asn Thr Phe Gly Gly Gly Thr Lys Val Glu Ile Lys
            100                 105                 110

<210> SEQ ID NO 31
<211> LENGTH: 13
<212> TYPE: PRT
<213> ORGANISM: Artificial
<220> FEATURE:
<223> OTHER INFORMATION: light chain CDR1, Mab ra170 10.12 and 11.12

<400> SEQUENCE: 31

Arg Ser Ser Gln Ser Val Gly Asn Asn Asn Asp Leu Ala
1               5                   10

<210> SEQ ID NO 32
<211> LENGTH: 7
<212> TYPE: PRT
<213> ORGANISM: Artificial
<220> FEATURE:
<223> OTHER INFORMATION: light chain CDR2, Mab ra170 10.12 and 11.12

<400> SEQUENCE: 32

Lys Ala Ser Thr Arg Ala Thr
1               5

<210> SEQ ID NO 33
<211> LENGTH: 11
<212> TYPE: PRT
<213> ORGANISM: Artificial
<220> FEATURE:
<223> OTHER INFORMATION: light chain CDR3, Mab ra170 10.12 and 11.12

<400> SEQUENCE: 33

Leu Gly Gly Tyr Asp Asp Asp Ala Asp Asn Thr
```

```
<210> SEQ ID NO 34
<211> LENGTH: 107
<212> TYPE: PRT
<213> ORGANISM: homo sapiens

<400> SEQUENCE: 34

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

ANTIBODIES AGAINST HUMAN IL33R AND USES THEREOF

CROSS-REFERENCE TO RELATED APPLICATIONS

The present application claims of priority under 35 USC §119(a) to European patent application number EP11155684.1, filed 23 Feb. 2011, the contents of which is incorporated herein by reference.

SEQUENCE LISTING

A sequence listing comprising SEQ ID NOS: 1-34 is attached hereto. Each sequence provided in the sequence listing is incorporated herein by reference, in its entirety, for all purposes.

TECHNICAL FIELD

The present invention relates to antibodies against human IL33R (IL33R antibody), methods for their production, pharmaceutical compositions containing said antibodies, and uses thereof.

BACKGROUND OF THE INVENTION

Human IL33 is an interleukin-1-like cytokine of the IL-1 family that signals via the IL-1 receptor-related IL33 receptor (synonyms of the receptor: IL1RL1, T1/ST2) and induces T helper type 2-associated cytokines. Synonyms of IL33 (Swiss-Prot Acc. No. O95760) are interleukin-1 family member 11 (IL-1F11) and nuclear factor from high endothelial venules (NF-HEV). NF-HEV is described in Baekkevold, E. S., et al., Am. J. Pathol. 163 (2003) 69-79. IL33 is described by Schmitz, J., et al., Immunity 23 (2005) 479-490.

Human IL33 Receptor, IL33R, (synonym for ILRL1; SwissProt Acc No. Q01638, other names are ST2, T1/ST2, Fit-1 and DER4) is induced by growth stimulation in fibroblastic cells, and can also be induced by antigen stimulation in Th2 cells. According to the invention IL33R and ST2 denotes human IL33R. Tominaga, S., et al., (FEBS Lett. 258 (1989) 301-304; Biochim. Biophys. Acta. 1171 (1992) 215-218) and Yanagisawa, K., (FEBS Lett. 318 (1993) 83-87) identified human ST2 (the secreted form), ST2L (the transmembrane receptor form) and ST2V (variant Glu-78). Human ST2 is only expressed in growth-stimulated BALB/c-3T3 cells and a member of the primary response gene family induced by growth factors. ST2 encodes a protein similar in sequence to the extracellular portion of human interleukin 1 receptor, both types 1 and 2. Studies with IL33R knockout mice suggest that IL33R is involved in early events of Th2-response (Kropf, P., et al., Infect. Immunity 70 (2002) 5512-5520; Hoshino, K., et al., J. Exp. Med. 190 (1999) 1541-1548; Senn, et al., Eur. J. Immunol. 30 (2000) 1929-1938; Townsend, M. J., et al., J. Exp. Med. 191 (2000) 1069-1076). ST2 is assumed to be a marker, activator and regulator of Th2 immunity (Kumar, R. K., et al., Clin. Exp. Allergy 32 (2002) 1394-1396).

Anti-IL33R antibodies and their role in immune function were described in a number of publications. Anti-human ST2 antibody Mab523 and polyclonal antibody AF523 are commercially availably from R&D Systems (which can be found on the world wide web with a URL address of rndsystems.com). Anti-human ST2 antibody HB12 is commercially availably from antibodies-online GmbH, Germany and MBL Int. Corp. (which can be found on the world wide web with a URL address of mblintl.com). Anti-IL33R antibodies resulted in decreased Th2-type immune responses. The antibody inhibited eosinophil infiltration, IL-5 production, and IgE-production. The evaluation of the role of ST2 in animal models for asthma resulted in increased expression of murine IL33R on CD4+ T cells, indicating a role for IL33R in allergic or asthmatic responses (Löhning, M., et al., Proc. Natl. Acad. Sci. USA 95 (1998) 6930-6935 and Xu, D., et al., J. Exp. Med. 187 (1998) 787-794; Coyle, A. J., et al., J. Exp. Med. 190 (1999) 895-902). Meisel, C., et al., J. Immunol. 166 (2001) 3143-3150 investigate the regulation and function of T1/ST2 expression on CD4$^+$ T cells and the induction of type 2 cytokine production by T1/ST2 cross-linking. Löhning, M., et al., generate an anti-mouse ST2 antibody in rats. Pretreatment with 20 μg (approx 0.0.8 mg/kg) of such an antibody 1 hr before allergen provocation reduced the number of eosinophils in the mouse airway by 70%. Kumar, S., et al., (Biochem. Biophys. Res. Comm. 235 (1997) 474-478 and J. Biol. Chem. 270 (1995) 27905-27913) describe the expression of ST2 protein detected by immunoprecipitation using a rabbit polyclonal antibody generated against purified soluble ST2 receptor expressed in *Drosophila*. Studies with BALB/c mice revealed that treating with anti-IL33 antibody induced higher Th1-type response. An ELISA system to quantify human ST2 protein in sera of patients was described by Kuroiwa, K., et al., Hybridoma 19 (2000) 151-159. Anti-IL33R antibodies also reduce effects due to infections with RSV (Walzl, et al., J. Exp. Med. 193 (2001) 785-792). Anti-IL33R antibodies were also investigated in an animal model of arthritis (Leung, B. P., et al., J. Immunol. 173 (2004) 145-150; Walzl, et al., J. Exp. Med. 193 (2001) 785-792). Smithgall, M. D., et al., Int. Immunol. 20 (2008) 1019-1030 investigated interferon γ levels in NK cells in the presence of an anti-huST2 antibody. IL33R and/or antibodies against IL33R are mentioned in WO 2005/079844, U.S. Pat. No. 7,087,396, WO 2001/021641, WO 2002/038794, WO 2003/094856. Oboki, K., et al., Allergology Int. 59 (2010) 143-160, review the role of IL33 and IL33 receptors in host defense and diseases and the effects of anti-ST2 antibody, soluble ST2 and anti-IL33 antibody on mouse airway inflammation.

SUMMARY OF THE INVENTION

The invention comprises an antibody binding to IL33R, characterized in that the heavy chain variable domain comprises a CDR3 region of SEQ ID NO:1, a CDR2 region of SEQ ID NO:2 and a CDR1 region of SEQ ID NO:3 and in that the light chain variable domain comprises a CDR3 region of SEQ ID NO:4, a CDR2 region of SEQ ID NO:5 and a CDR1 region of SEQ ID NO:6. Preferably the antibody is characterized in that the heavy chain variable domain comprises SEQ ID NO:7. Preferably the antibody is characterized in that the heavy chain variable domain comprises SEQ ID NO:7 and the light chain variable domain comprises SEQ ID NO:8. Preferably the antibody binding to IL33R and being characterized by the above mentioned amino acid sequences and amino acid sequence fragments is of human IgG1 isotype modified in the hinge region at amino acid position 216-240, preferably at amino acid position 220-240, between $C_H1$ and $C_H2$ and/or in the second inter-domain region at amino acid position 327-331 between $C_H2$ and $C_H3$. Preferably the antibody comprises mutations L234A (alanine instead of leucine at amino acid position 234) and L235A. A preferred heavy chain constant region including mutations L234A and L235A is shown in SEQ ID NO:9. Preferably the antibody binding to IL33R and being characterized by the above mentioned amino acid sequences and amino acid sequence fragments is of human IgG4 isotype modified in the hinge region at amino acid position 216-240, preferably at amino acid position 220-240, between $C_H1$ and $C_H2$ and/or in the second inter-domain region at amino acid position 327-331 between $C_H2$ and $C_H3$. Preferably the antibody comprises mutations L235E (glutamic acid instead of leucine at amino acid position 235) and S228P (proline instead of serine at amino acid position 228).

Antibody ra170 (Mab ra170) is a preferred embodiment of the invention. A further embodiment of the invention is a chimeric, humanized or T cell epitope depleted antibody variant of antibody ra170.

Preferred humanized antibody variants of antibody ra170 are characterized in that the heavy chain variable domain comprises a CDR3 region of SEQ ID NO: 24, a CDR2 region of SEQ ID NO:23 and a CDR1 region of SEQ ID NO:22 and in that the light chain variable domain comprises a CDR3 region of SEQ ID NO: 33, a CDR2 region of SEQ ID NO:32 and a CDR1 region of SEQ ID NO:31, or are characterized in that the heavy chain variable domain comprises a CDR3 region of SEQ ID NO: 28, a CDR2 region of SEQ ID NO:27 and a CDR1 region of SEQ ID NO:26 and in that the light chain variable domain comprises a CDR3 region of SEQ ID NO: 33, a CDR2 region of SEQ ID NO:32 and a CDR1 region of SEQ ID NO:31. Preferably the humanized antibody is characterized in that the heavy chain variable domain comprises SEQ ID NO:21 or 25. Preferably the humanized antibody is characterized in that the light chain variable domain comprises SEQ ID NO:30.

The antibody binds specifically to IL33R with an affinity of $10^{-10}$M or lower.

The invention relates further to an antibody binding to IL33R and being characterized by binding to the same IL33R epitope to which monoclonal antibody ra170 binds. The antibody binds to IL33R with an affinity of at least $10^{-8}$ $M^{-1}$ to $10^{-12}$ $M^{-1}$, is preferably of human IgG1 isotype modified in the hinge region at amino acid position 216-240, preferably at amino acid position 220-240, between $C_H1$ and $C_H2$ and/or in the second inter-domain region at amino acid position 327-331 between $C_H2$ and $C_H3$. Preferably the antibody is of human IgG1 isotype comprising mutations L234A and L235A or of human IgG4 isotype comprising mutations L235E and S228P.

Preferably the antibody is a humanized or human antibody. Preferably the antibody according to the invention inhibits binding of IL33 to IL33R with an IC50 value of 0.32 nM for human IL33/IL33R and 0.13 nM for cynomolgus IL33/IL33R.

Antibodies according to the invention preferably show $IC_{50}$ values of 5 nM or lower in the eosoinophil assay, mast cell assay, Th2 assay, basophil assay (IL-5), Such antibodies are especially useful in the treatment of rheumatoid arthritis, asthma or ulcerative colitis.

A further embodiment of the invention is a pharmaceutical composition comprising an antibody according to the invention. Preferably the pharmaceutical composition comprises an antibody characterized by binding to the same IL33R epitope to which monoclonal antibody ra170 binds. Preferably the antibody of the pharmaceutical composition binds to IL33R with an affinity of at least $10^{-8}$ $M^{-1}$ to $10^{-12}$ $M^{-1}$, is preferably of human IgG1 isotype modified in the hinge region at amino acid position 216-240, preferably at amino acid position 220-240, between $C_H1$ and $C_H2$ and/or in the second inter-domain region at amino acid position 327-331 between $C_H2$ and $C_H3$. Preferably the antibody is of human IgG1 isotype comprising mutations L234A (alanine instead of leucine at amino acid position 234) and L235A or of human IgG4 isotype comprising mutations L235E and S228P.

A further embodiment of the invention is the use of an antibody according to the invention for the manufacture of a pharmaceutical composition. Preferably the pharmaceutical composition comprises an antibody characterized by binding to the same IL33R epitope to which monoclonal antibody ra170 binds. Preferably the antibody of the pharmaceutical composition binds to IL33R with an affinity of at least $10^{-8}$ $M^{-1}$ to $10^{-12}$ $M^{-1}$, is preferably of human IgG1 isotype modified in the hinge region at amino acid position 216-240, preferably at amino acid position 220-240, between $C_H1$ and $C_H2$ and/or in the second inter-domain region at amino acid position 327-331 between $C_H2$ and $C_H3$. Preferably the antibody is of human IgG1 isotype comprising mutations L234A (alanine instead of leucine at amino acid position 234) and L235A or is of human IgG4 isotype comprising mutations L235E and S228P.

A further embodiment of the invention is the use of an antibody according to the invention for the treatment of ulcerative colitis or asthma. A further embodiment of the invention is a method for the manufacture of a pharmaceutical composition comprising an antibody according to the invention. Preferably the pharmaceutical composition comprises an antibody characterized by binding to the same IL33R epitope to which monoclonal antibody ra170 binds. Preferably the antibody of the pharmaceutical composition binds to IL33R with an affinity of at least $10^{-8}$ $M^{-1}$ to $10^{-12}$ $M^{-1}$, is preferably of human IgG1 isotype modified in the hinge region at amino acid position 216-240, preferably at amino acid position 220-240, between $C_H1$ and $C_H2$ and/or in the second inter-domain region at amino acid position 327-331 between $C_H2$ and $C_H3$. Preferably the antibody is of human IgG1 isotype comprising mutations L234A (alanine instead of leucine at amino acid position 234) and L235A or is of human IgG4 isotype comprising mutations L235E and S228P.

A further embodiment of the invention is a nucleic acid encoding a heavy chain of an antibody binding to IL33R, characterized in comprising a heavy chain CDR3 region of SEQ ID NO:1 and preferably mutations L234A and L235A in the IgG1 heavy chain constant domain. Preferably the antibody comprises in addition a heavy chain CDR2 region of SEQ ID NO:2 and a CDR1 region of SEQ ID NO:3. A further embodiment of the invention is a nucleic acid encoding a light chain of an antibody binding to IL33R, characterized by comprising a light chain CDR3 region of SEQ ID NO:4 and preferably mutations L234A and L235A in the IgG1 heavy chain constant domain. Preferably the antibody comprises in addition a light chain CDR2 region of SEQ ID NO:5 and a CDR1 region of SEQ ID NO:6. A further embodiment of the invention is a nucleic acid encoding an antibody according to the invention characterized by comprising a heavy chain variable domain of SEQ ID NO: 7 and a variable light chain domain of SEQ ID NO:8 and preferably mutations L234A and L235A in the heavy chain human IgG1 constant domain or mutations L235E and S228P in the heavy chain human IgG4 constant domain.

A further embodiment of the invention is a nucleic acid encoding a heavy chain of an antibody binding to IL33R, characterized in comprising a heavy chain CDR3 region of SEQ ID NO:24 and preferably mutations L234A and L235A in the IgG1 heavy chain constant domain. Preferably the antibody comprises in addition a heavy chain CDR2 region of SEQ ID NO:23 and a CDR1 region of SEQ ID NO:22. A further embodiment of the invention is a nucleic acid encoding a light chain of an antibody binding to IL33R, characterized by comprising a light chain CDR3 region of SEQ ID NO:33 and preferably mutations L234A and L235A in the IgG1 heavy chain constant domain. Preferably the antibody comprises in addition a light chain CDR2 region of SEQ ID NO:2 and a CDR1 region of SEQ ID NO:31. A further embodiment of the invention is a nucleic acid encoding an antibody according to the invention characterized by comprising a heavy chain variable domain of SEQ ID NO: 21 and a variable light chain domain of SEQ ID NO:30 and preferably mutations L234A and L235A in the heavy chain human IgG1 constant domain or mutations L235E and S228P in the heavy chain human IgG4 constant domain.

A further embodiment of the invention is a nucleic acid encoding a heavy chain of an antibody binding to IL33R, characterized in comprising a heavy chain CDR3 region of SEQ ID NO:28 and preferably mutations L234A and L235A in the IgG1 heavy chain constant domain. Preferably the antibody comprises in addition a heavy chain CDR2 region of SEQ ID NO:27 and a CDR1 region of SEQ ID NO:26. A further embodiment of the invention is a nucleic acid encoding a light chain of an antibody binding to IL33R, characterized by comprising a light chain CDR3 region of SEQ ID NO:33 and preferably mutations L234A and L235A in the IgG1 heavy chain constant domain. Preferably the antibody comprises in addition a light chain CDR2 region of SEQ ID NO:2 and a CDR1 region of SEQ ID NO:31. A further embodiment of the invention is a nucleic acid encoding an antibody according to the invention characterized by comprising a heavy chain variable domain of SEQ ID NO: 25 and a variable light chain domain of SEQ ID NO:30 and preferably mutations L234A and L235A in the heavy chain human IgG1 constant domain or mutations L235E and S228P in the heavy chain human IgG4 constant domain.

The antibody according to the invention is preferably characterized in that the constant chains are of human origin. Such constant chains are well known in the state of the art and e.g., described by Kabat (Kabat, E. A., et al., Sequences of Proteins of Immunological Interest, 5th ed., Public Health Service, National Institutes of Health, Bethesda, Md. (1991), and Johnson, G. and Wu, T. T., Nucleic Acids Res. 28 (2000) 214-218). For example, a useful human heavy chain constant region comprises an amino acid sequence of SEQ ID NO: 9 (human IgG1 including the mutations L234A and L235A) or of SEQ ID NO: 29 (human IgG4 including the mutations L235E and S228P). For example, a useful human light chain constant region comprises an amino acid sequence of a kappa-light chain constant region of SEQ ID NO: 12 or 34. It is further preferred that the antibody is of mouse origin and comprises the antibody variable sequence frame of a mouse antibody according to Kabat (Kabat, E. A., et al., Sequences of Proteins of Immunological Interest, 5th ed., Public Health Service, National Institutes of Health, Bethesda, Md. (1991); and Johnson, G. and Wu, T. T., Nucleic Acids Res. 28 (2000) 214-218).

The antibody according to the invention is especially characterized by inhibiting the binding of IL33 to IL33R and therefore of inhibiting signaling via IL33R/IL-1RacP signaling complex.

The antibody according to the invention is preferably of human isotype IgG1. Preferred γ1 heavy chain constant regions are shown in SEQ ID NO:10 or 29 and in SEQ ID NO:11 without L234A and L235A mutations. A preferred K light chain constant region is shown in SEQ ID NO:12 or 34.

The antibody according to the invention is preferably characterized by not binding human complement factor C1q and avoid therefore CDC effector function.

The antibody according to the invention is preferably of human IgG1 isotype modified in the hinge region at amino acid position 216-240, preferably at amino acid position 220-240, between $C_H1$ and $C_H2$ and/or in the second inter-domain region at amino acid position 327-331 between $C_H2$ and $C_H3$. The antibody according to the invention is preferably characterized by being of human IgG1 isotype, containing at least one mutation in, L234 (leucine at amino acid position 234), L235, D270, N297, E318, K320, K322, P331, and/or P329 (numbering according to EU index). Preferably the antibody is of human IgG1 isotype comprising mutations L234A (alanine instead of leucine at amino acid position 234) and L235A or is of human IgG4 isotype comprising mutations L235E and S228P.

The invention further provides expression vectors containing nucleic acid according to the invention capable of expressing said nucleic acid in a prokaryotic or eukaryotic host cell, and host cells containing such vectors for the recombinant production of such an antibody. The invention further comprises a prokaryotic or eukaryotic host cell comprising a vector according to the invention. The invention further comprises a method for the production of a recombinant human or humanized antibody according to the invention, characterized by expressing a nucleic acid according to the invention in a prokaryotic or eukaryotic host cell and recovering said antibody from said cell or the cell culture supernatant. The invention further comprises the antibody obtainable by such a recombinant method.

Antibodies according to the invention show benefits for patients in need of an IL33R targeting therapy. The antibodies according to the invention have new and inventive properties causing especially a benefit for a patient suffering from such an immunological disease, especially suffering from rheumatoid arthritis, ulcerative colitis or asthma. The antibodies according to the invention are not causing susceptibility for staphylococcal and enteric bacterial infections of the treated patient. The invention further provides a method for treating a patient suffering from rheumatoid arthritis, ulcerative colitis or asthma comprising administering to a patient diagnosed as having such a disease (and therefore being in need of such a therapy) an effective amount of an antibody binding to IL33R according to the invention. The antibody is administered preferably in a pharmaceutical composition. A further embodiment of the invention is a method for the treatment of a patient suffering from rheumatoid arthritis, ulcerative colitis or asthma, characterized by administering to the patient an antibody according to the invention. The invention further comprises the use of an antibody according to the invention for the treatment of a patient suffering from rheumatoid arthritis, ulcerative colitis or asthma and for the manufacture of a pharmaceutical composition according to the invention. In addition, the invention comprises a method for the manufacture of a pharmaceutical composition according to the invention.

The invention further comprises a pharmaceutical composition comprising an antibody according to the invention, optionally together with a buffer and/or an adjuvant useful for the formulation of antibodies for pharmaceutical purposes. The invention further provides pharmaceutical compositions comprising an antibody according to the invention in a pharmaceutically acceptable carrier. In one embodiment, the pharmaceutical composition may be included in an article of manufacture or kit.

DETAILED DESCRIPTION OF THE INVENTION

The term "antibody" encompasses the various forms of antibody structures including but not being limited to whole antibodies and antibody fragments. The antibody according to the invention is preferably a humanized antibody, chimeric antibody, or further genetically engineered antibody as long as the characteristic properties according to the invention are retained. "Antibody fragments" comprise a portion of a full length antibody, preferably the variable domain thereof, or at least the antigen binding site thereof. Examples of antibody fragments include diabodies, single-chain antibody molecules, and multispecific antibodies formed from antibody fragments. scFv antibodies are, e.g., described in Huston, J. S., Methods in Enzymol. 203 (1991) 46-88. In addition, antibody fragments comprise single chain polypeptides having the characteristics of a $V_H$ domain, namely being able to assemble together with a $V_L$ domain, or of a $V_L$ domain binding to IL33R, namely being able to assemble together with a $V_H$ domain to a functional antigen binding site and thereby providing the properties of an antibody according to the invention. The terms "monoclonal antibody" or "monoclonal antibody composition" as used herein refer to a preparation of antibody molecules of a single amino acid composition. The term "humanized antibody" refers to antibodies in which the framework and/or "complementary determining regions" (CDR) have been modified to comprise the CDR of an immunoglobulin of different species as compared to that of the parent immunoglobulin. In a preferred embodiment, a mouse CDR is grafted into the framework region of a human antibody to prepare the "humanized antibody". See, e.g., Riechmann, L., et al., Nature 332 (1988) 323-327; and Neuberger, M. S., et al., Nature 314 (1985) 268-270.

The term "binding to IL33R" as used herein means binding of the antibody to immobilized human IL33R in an ELISA binding assay. Binding is found if the antibody causes a signal greater than average+3 standard deviations or more of the control without antibody at an antibody concentration of greater than 12 ng/ml.

The term "affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

The term "epitope" denotes a protein determinant capable of specifically binding to an antibody. Epitopes usually consist of chemically active surface groupings of molecules such as amino acids or sugar side chains and usually epitopes have specific three dimensional structural characteristics, as well as specific charge characteristics. Conformational and non-conformational epitopes are distinguished in that the binding to the former but not the latter is lost in the presence of denaturing solvents. Preferably an antibody according to the invention binds specifically to native but not to denatured IL33R. The IL33R antibody of the invention binds to the same epitope on IL33R to which antibody Mab ra170 binds. The epitope binding property of an IL33R antibody of the present invention may be determined using techniques known in the art. The IL33R antibody is tested by an in vitro cross-blocking binding assay to determine the ability of the test antibody to hinder the binding of antibody Mab ra170 to IL33R. If there is a displacement of the test antibody by antibody Mab ra170 for at least 15%, then the epitopes are in near proximity.

The "variable domain" (variable domain of a light chain ($V_L$), variable domain of a heavy chain ($V_H$)) as used herein denotes each of the pair of light and heavy chain domains which are involved directly in binding of the antibody to the antigen. The variable light and heavy chain domains have the same general structure and each domain comprises four framework (FR) regions whose sequences are widely conserved, connected by three "hypervariable regions" (or complementary determining regions, CDRs). The framework regions adopt a (β-sheet conformation and the CDRs may form loops connecting the β-sheet structure. The CDRs in each chain are held in their three-dimensional structure by the framework regions and form together with the CDRs from the other chain the antigen binding site. The antibody's heavy and light chain CDR3 regions play a particularly important role in the binding specificity/affinity of the antibodies according to the invention and therefore provide a further object of the invention.

The term "antigen-binding portion of an antibody" when used herein refers to the amino acid residues of an antibody which are responsible for antigen-binding. The antigen-binding portion of an antibody comprises amino acid residues from the "complementary determining regions" or "CDRs". "Framework" or "FR" regions are those variable domain regions other than the hypervariable region residues as herein defined. Therefore, the light and heavy chain variable domains of an antibody comprise from N- to C-terminus the domains FR1, CDR1, FR2, CDR2, FR3, CDR3, and FR4. Especially, CDR3 of the heavy chain is the region which contributes most to antigen binding and defines the antibody's properties. CDR and FR regions are determined according to the standard definition of Kabat, et al., Sequences of Proteins of Immunological Interest, 5th ed., Public Health Service, National Institutes of Health, Bethesda, Md. (1991) and/or those residues from a "hypervariable loop".

The term "amino acid" as used within this application denotes the group of naturally occurring carboxy-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

The terms "nucleic acid" or "nucleic acid molecule", as used herein, are intended to include DNA molecules and RNA molecules. A nucleic acid molecule may be single-stranded or double-stranded, but preferably is double-stranded DNA. A nucleic acid is "operably linked" when it is placed into a functional relationship with another nucleic acid. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operable linked" means that the DNA sequences being linked are colinear, and, in the case of a secretory leader, contiguous and in reading frame. However, enhancers do not have to be contiguous. Linking is accomplished by ligation at convenient restriction sites. If such sites do not exist, synthetic oligonucleotide adaptors or linkers are used in accordance with conventional practice. As used herein, the expressions "cell", "cell line", and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

The "Fc part" of an antibody is not involved directly in binding of an antibody to an antigen, but exhibits various effector functions. An "Fc part of an antibody" is a term well known to the skilled artisan and defined on the basis of papain cleavage of antibodies. Depending on the amino acid sequence of the constant region of their heavy chains, antibodies or immunoglobulins are divided in the classes: IgA, IgD, IgE, IgG and IgM, and several of these may be further divided into subclasses (isotypes), e.g., IgG1, IgG2, IgG3, and IgG4, IgA1, and IgA2. According to the heavy chain constant regions the different classes of immunoglobulins are called α, δ, ε, γ, and μ respectively. The Fc part of an antibody is directly involved in ADCC (antibody-dependent cell-mediated cytotoxicity) and CDC (complement-dependent cytotoxicity) based on complement activation, C1q binding and Fc receptor binding. Complement activation (CDC) is initiated by binding of complement factor C1q to the Fc part of most IgG antibody subclasses. While the influence of an antibody on the complement system is dependent on certain conditions, binding to C1q is caused by defined binding sites in the Fc part. Such binding sites are known in the state of the art and described by, e.g., Boackle, R. J., et al., Nature 282 (1979) 742-743; Lukas, T. J., et al., J. Immunol. 127 (1981) 2555-2560; Brunhouse, R. and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M., et al., J. Virology 75 (2001) 12161-12168; Morgan, A., et al., Immunology 86 (1995) 319-324; EP 0 307 434. Such binding sites are, e.g., L234, L235, D270, N297, E318, K320, K322, P331, and P329 (numbering according to EU index of Kabat, Kabat, E. A., et al., Sequences of Proteins of Immunological Interest, 5th ed., Public Health Service, National Institutes of Health, Bethesda, Md. (1991)). Antibodies of subclass IgG1, IgG2 and IgG3 usually show complement activation and C1q binding, whereas IgG4 does not activate the complement system and does not bind C1q.

The antibody according to the invention comprises an Fc part from human origin which is Fc part of a human antibody of the subclass IgG1 or IgG4. For the Fc part of an antibody according to the invention preferably no C1q binding as defined below can be detected.

The invention therefore comprises an antibody according to the invention, characterized in that said antibody binds IL33R, contains an Fc part from human origin, and does not bind human complement factor C1q and therefore avoids CDC effector function.

Preferably an antibody according to the invention is in regard to Fcγ receptor binding of human IgG1 or IgG2 subclass, with a mutation in L234, L235, and/or D265, and/or contains the PVA236 mutation. Preferred are the mutations L234A, L235A, L235E, and/or PVA236 (PVA236 means that the amino acid sequence ELLG (given in one letter amino acid code) from amino acid position 233 to 236 of IgG1 or EFLG of IgG4 is replaced by PVA). The present invention thus provides an antibody according to the invention being characterized in that said antibody is an antibody of human subclass IgG1, containing at least one mutation in L234, L235, D270, N297, E318, K320, K322, P331 and/or P329. In one embodiment the antibody is a human antibody. In another embodiment the antibody is a humanized antibody. In one embodiment the present invention provides an antibody according to the invention, containing an Fc part derived from human origin, and being characterized in that said antibody is an antibody of human subclass IgG1, containing at least one mutation in L234, L235, D270, N297, E318, K320, K322, P331 and wherein the antibody binds to IL33R with a $K_D$ value of less than $10^{-8}$ M in a BIAcore assay. In another embodiment the $K_D$ range is $10^{-11}$ to $10^{-9}$ M.

C1q binding can be measured according to Idusogie, E. E., et al., J. Immunol. 164 (2000) 4178-4184. No C1q binding according to the invention is characterized in that if in such an assay wherein an ELISA plate is coated with different concentrations of the antibody, human C1q is added. C1q binding is detected by an antibody directed against human C1q followed by peroxidase-labeled conjugate detection with peroxidase substrate ABTS® (2,2'-Azino-di-[3-ethylbenzthiazolinesulfonate]). No C1q binding according to the invention is found if the optical density (OD) at 405 nm is for the test antibody lower than 0.05 at an antibody concentration of 10 μg/ml.

The antibody according to the invention is preferably characterized in that the constant chains are of human origin. Such constant chains are well known in the state of the art and described, e.g., by Kabat (Kabat, E. A., et al., Sequences of Proteins of Immunological Interest, 5th ed., Public Health Service, National Institutes of Health, Bethesda, Md. (1991); and Johnson, G., and Wu, T. T., Nucleic Acids Res. 28 (2000) 214-218). For example, a useful human heavy chain constant region comprises SEQ ID NO: 10, 11 or 29. For example, a useful human light chain constant region comprises an amino acid sequence of a kappa-light chain constant region of SEQ ID NO: 12 or 34.

A further embodiment of the invention is a nucleic acid encoding a heavy and a light chain of an antibody according to the invention.

The invention comprises a method for the treatment of a patient in need of therapy, characterized by administering to the patient a therapeutically effective amount of an antibody according to the invention. The invention comprises the use of an antibody according to the invention for therapy. The invention comprises the use of an antibody according to the invention for the preparation of a medicament for the prophylaxis and treatment especially of inflammatory disorders. The invention comprises the use of an antibody according to the invention for the treatment of inflammatory diseases, preferably for the treatment of rheumatoid arthritis, ulcerative colitis and asthma.

The antibodies according to the invention include, in addition, such antibodies having "conservative sequence modifications" (variant antibodies), nucleotide and amino acid sequence modifications which do not affect or alter the above-mentioned characteristics of the antibody according to the invention. Modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

Thus, a predicted nonessential amino acid residue in a human anti-IL33R antibody can be preferably replaced with another amino acid residue from the same side chain family. A "variant" anti-IL33R antibody, refers therefore herein to a molecule which differs in amino acid sequence from a "parent" anti-IL33R antibody amino acid sequence by up to ten, preferably from about two to about five, additions, deletions and/or substitutions in one or more variable region of the parent antibody. Amino acid substitutions can be performed by mutagenesis based upon molecular modeling as described by Riechmann, L., et al., Nature 332 (1988) 323-327 and Queen, C., et al., Proc. Natl. Acad. Sci. USA 86 (1989) 10029-10033.

A further embodiment of the invention is a method for the production of an antibody against IL33R which does not bind Fcγ receptor and/or C1q, characterized in that the sequence of a nucleic acid encoding the heavy chain of a human IgG1 type antibody binding to IL33R is modified in such a manner that said modified antibody does not bind C1q and/or Fcγ receptor, said modified nucleic acid and the nucleic acid encoding the light chain of said antibody are inserted into an expression vector, said vector is inserted in a eukaryotic host cell, the encoded protein is expressed and recovered from the host cell or the supernatant.

Identity or homology with respect to the sequence is defined herein as the percentage of amino acid residues in the candidate sequence that are identical with the parent sequence, after aligning the sequences and introducing gaps, if necessary, to achieve the maximum percent sequence identity. None of N-terminal, C-terminal, or internal extensions, deletions, or insertions into the antibody sequence shall be construed as affecting sequence identity or homology. The variant retains the ability to bind human IL33R and preferably has properties, which are superior to those of the parent antibody. For example, the variant may have reduced side effects during treatment.

The "parent" antibody comprises the CDR regions of antibody ra170 and is preferably used for the preparation of the variant. Preferably, the parent antibody has a human framework region and, if present, has a human antibody constant region or human antibody constant domains. For example, the parent antibody may be a humanized or a human antibody.

The antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression nucleic acids encoding light and heavy chains or fragments thereof are inserted into expression vectors by standard methods. Expression is performed in appropriate prokaryotic or eukaryotic host cells, such as CHO cells, NS0 cells, SP2/0 cells, HEK293 cells, COS cells, yeast, or E. coli cells, and the antibody is recovered from the cells (from the supernatant or after cells lysis). Recombinant production of antibodies is well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-160; Werner, R. G., Drug Res. 48 (1998) 870-880. The antibodies may be present in whole cells, in a cell lysate, or in a partially purified, or substantially pure form. Purification is performed in order to eliminate other cellular components or other contaminants, e.g., other cellular nucleic acids or proteins, by standard techniques, including column chromatography and others well known in the art. See Ausubel, F., et al., ed., Current Protocols in Molecular Biology, Greene Publishing and Wiley Interscience, New York (1987). Expression in NS0 cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; Norderhaug, L., et al., J. Immunol. Methods 204 (1997) 77-87. A preferred transient expression system (HEK 293) is described by Schlaeger, E.-J. and Christensen, K., in Cytotechnology 30 (1999) 71-83, and by Schlaeger, E.-J., in J. Immunol. Methods 194 (1996) 191-199. Monoclonal antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells, such as HEK 293 cells, CHO cells, or myeloma cells that do not otherwise produce immunoglobulin protein, to obtain the synthesis of recombinant monoclonal antibodies in the host cells.

Amino acid sequence variants of human IL33R antibody are prepared by introducing appropriate nucleotide changes into the antibody encoding DNA, or by peptide synthesis. Such modifications can be performed, however, only in a very limited range, e.g., as described above. For example, the modifications do not alter the above-mentioned antibody characteristics such as the IgG isotype and epitope binding, but may improve the yield of the recombinant production, protein stability, or facilitate the purification. Any cysteine residue not involved in maintaining the proper conformation of the anti-IL33R antibody may also be substituted, generally with serine, to improve the oxidative stability of the molecule and to prevent aberrant crosslinking. Conversely, cysteine bond(s) may be added to the antibody to improve its stability (particularly where the antibody is an antibody fragment such as an Fv fragment). Another type of amino acid variant of the antibody alters the original glycosylation pattern of the antibody. By "altering" is meant removing one or more carbohydrate moieties found in the antibody and/or adding one or more glycosylation sites that are not present in the antibody. Glycosylation of antibodies is typically N-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites).

Nucleic acid molecules encoding amino acid sequence variants of anti-IL33R antibody are prepared by a variety of methods known in the art. These methods include, but are not limited to, isolation from a natural source (in the case of naturally occurring amino acid sequence variants) or preparation by oligonucleotide-mediated (or site-directed)

mutagenesis, PCR mutagenesis, and cassette mutagenesis of an earlier prepared variant or a non-variant version of humanized anti-IL33R antibody.

Another type of covalent modification of the antibody comprises linking the antibody to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192; 4,179,337.

The heavy and light chain variable domains according to the invention are combined with sequences of promoter, translation initiation, constant region, 3' untranslated region, polyadenylation, and transcription termination to form expression vector constructs. The heavy and light chain expression constructs can be combined into a single vector, co-transfected, serially transfected, or separately transfected into host cells which are then fused to form a single host cell expressing both chains.

In another aspect, the present invention provides a composition, e.g., a pharmaceutical composition, containing one or a combination of monoclonal antibodies, or the antigen-binding portion thereof, of the present invention, formulated together with a pharmaceutically acceptable carrier. As used herein, "pharmaceutically acceptable carrier" includes any and all solvents, dispersion media, coatings, antibacterial and antifungal agents, isotonic and absorption/resorption delaying agents, and the like that are physiologically compatible. Preferably, the carrier is suitable for injection or infusion. A composition of the present invention can be administered by a variety of methods known in the art. As will be appreciated by the skilled artisan, the route and/or mode of administration will vary depending upon the desired results. Pharmaceutically acceptable carriers include sterile aqueous solutions or dispersions and sterile powders for the preparation of sterile injectable solutions or dispersion. The use of such media and agents for pharmaceutically active substances is known in the art. In addition to water, the carrier can be, for example, an isotonic buffered saline solution. Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art. Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient (effective amount). The selected dosage level will depend upon a variety of pharmacokinetic factors including the activity of the particular compositions of the present invention employed, or the ester, salt or amide thereof, the route of administration, the time of administration, the rate of excretion of the particular compound being employed, other drugs, compounds and/or materials used in combination with the particular compositions employed, the age, sex, weight, condition, general health and prior medical history of the patient being treated, and like factors well known in the medical arts.

The invention comprises the use of the antibodies according to the invention for the treatment of a patient suffering from rheumatoid arthritis, ulcerative colitis or asthma.

A further embodiment of the invention is the use of an anti-IL33R antibody, preferably an antibody according to the invention, for the treatment of a patient suffering from rheumatoid arthritis, said patient do respond moderate or do not respond to the treatment with a TNF antagonist, anti-CD20 antibody, CTLA4Ig or anti-IL6 antibody. A further embodiment of the invention is the use of an anti-IL33R antibody, preferably an antibody according to the invention, for the manufacture of a medicament for the treatment of a patient suffering from rheumatoid arthritis, ulcerative colitis or asthma.

The invention further provides a method for the manufacture of a pharmaceutical composition comprising an effective amount of an antibody according to the invention together with a pharmaceutically acceptable carrier and the use of the antibody according to the invention for such a method. The invention further provides the use of an antibody according to the invention in an effective amount for the manufacture of a pharmaceutical agent, preferably together with a pharmaceutically acceptable carrier, for the treatment of a patient suffering from rheumatoid arthritis, ulcerative colitis or asthma. The invention also provides the use of an antibody according to the invention in an effective amount for the manufacture of a pharmaceutical agent, preferably together with a pharmaceutically acceptable carrier, for the treatment of a patient suffering from rheumatoid arthritis, ulcerative colitis or asthma.

DESCRIPTION OF THE SEQUENCES

SEQ ID NO: 1 heavy chain CDR3, Mab ra170
SEQ ID NO: 2 heavy chain CDR2, Mab ra170
SEQ ID NO: 3 heavy chain CDR1, Mab ra170
SEQ ID NO: 4 light chain CDR3, Mab ra170
SEQ ID NO: 5 light chain CDR2, Mab ra170
SEQ ID NO: 6 light chain CDR1, Mab ra170
SEQ ID NO: 7 heavy chain variable domain, Mab ra170
SEQ ID NO: 8 light chain variable domain, Mab ra170
SEQ ID NO: 9 human γ1 heavy chain constant region with mutations L234A and L235A (Caucasian Allotype)
SEQ ID NO: 10 human γ1 heavy chain constant region (Caucasian Allotype)
SEQ ID NO: 11 human γ1 heavy chain constant region (Afroamerican Allotype)
SEQ ID NO: 12 human κ light chain constant region
SEQ ID NO: 13 Replaced ST2 sequence fragment 1 for mut1
SEQ ID NO: 14 Replaced ST2 sequence fragment 2 for mut1
SEQ ID NO: 15 Replaced ST2 sequence fragment 3 for mut1
SEQ ID NO: 16 Replaced ST2 sequence fragment 4 for mut1
SEQ ID NO: 17 IL-1R fragment 1 mut1, replacing ST2 fragment SEQ13
SEQ ID NO: 18 IL-1R fragment 2 mut2, replacing ST2 fragment SEQ14
SEQ ID NO: 19 IL-1R fragment 3 mut3, replacing ST2 fragment SEQ15
SEQ ID NO: 20 IL-1R fragment 4 mut4, replacing ST2 fragment SEQ16
SEQ ID NO: 21 heavy chain variable domain, humanized ra170 11.12(VH11)
SEQ ID NO: 22 heavy chain CDR1, Mab ra170 11.12
SEQ ID NO: 23 heavy chain CDR2, Mab ra170 11.12
SEQ ID NO: 24 heavy chain CDR3, Mab ra170 11.12
SEQ ID NO: 25 heavy chain variable domain, humanized ra170 10.12(VH10)
SEQ ID NO: 26 heavy chain CDR1, Mab ra170 10.12
SEQ ID NO: 27 heavy chain CDR2, Mab ra170 10.12
SEQ ID NO: 28 heavy chain CDR3, Mab ra170 10.12
SEQ ID NO: 29 human IgG4 SPLE backbone (human γ4 heavy chain constant region with mutations L235E and S228P)
SEQ ID NO: 30 light chain variable domain, humanized ra170 (11.12 and 10.12)

SEQ ID NO: 31 light chain CDR1, Mab ra170 10.12 and 11.12
SEQ ID NO: 32 light chain CDR2, Mab ra170 10.12 and 11.12
SEQ ID NO: 33 light chain CDR3, Mab ra170 10.12 and 11.12
SEQ ID NO: 34 human kappa backbone

EXAMPLES

The present invention is described in further detain in the following examples which are not in any way intended to limit the scope of the invention as claimed. All references cited are herein specifically incorporated by reference for all that is described therein. The following examples are offered to illustrate, but not to limit the claimed invention.

Example 1

Immunization

Wildtype New Zealand White (NZW) Rabbits (*Oryctolagus cuniculus*) from Charles River Laboratories International, Inc. were used for immunization. They were housed and maintained according to the Institutional Animal Care and Use committee guidelines and Association for Assessment and Accreditation of Laboratory Animal Care (Germany, Europe).

Purified, NS0-derived, secreted soluble form of human IL33R fused to Fc region of human IgG was solved in NaCl-Histidin puffer pH 6.1 at a concentration of 1 mg/ml and mixed (1:1) with complete Freund's adjuvant (CFA) till generation of stabile emulsion. Three rabbits received an intra dermal (i.d.) injection of 2 ml of emulsion followed by a second intra muscular (i.m.) and third subcutaneous (s.c.) injection each with 1 ml in one week interval. The fourth i.m. injection of 1 ml was performed two weeks later followed by two further s.c. injections of 1 ml in four weeks interval. 10 ml peripheral whole blood samples of each animal was collected 4-6 days after third, fourth, fifth and sixth injection and used for single cell sorting in FACS. Additional 0.5 ml serum of each animal was collected at the same time and used for the characterization of IL33R specific antibody response.

Antibody_Response

The antibody response to the immunization was determined by serial dilution of sera using IL33R specific ELISA, in which 96-well MaxiSorp microtiter plates were coated with 0.3 µg/ml rhIL33R protein in carbonate buffer for 1 h at 37° C. Thereafter the wells were blocked with PBS supplemented with 1% Crotein C (Roche Diagnostics GmbH, DE) over night at 4° C. For detection, goat anti-rabbit IgG linked to a horseradish peroxidase (The Jackson Laboratory) was used at 1:16000 dilution. BM Blue POD Substrat, precipitating Tetramethylbenzidine (TMB), ready-to-use solution from Roche Diagnostics GmbH, DE, was used for visualization. Reaction was stopped via 1N HCl and measured in Tecan Infinite by 450/690 nm.

Description of Antibody Selection

Sterile cell culture 6-well plates were coated with 2 µg/ml IL33R protein in carbonate buffer (0.1 M sodium bicarbonate, 34 mM Disodiumhydrogencarbonate, pH 9.55) over night at 4° C. Plates were washed in sterile PBS three times before use. EDTA containing rabbit whole blood was diluted twofold with 1×PBS before density centrifugation on lympholyte mammal (Cedarlane Laboratories) which was performed to isolate rabbit PBMC. PBMCs were washed twice before staining with antibodies.

EL-4 B5 Medium

RPMI 1640 supplemented with 10% FCS (Hyclone, Logan, Utah, USA), 2 mM Glutamin, 1% penicillin/streptomycin solution, 2 mM sodium pyruvate, 10 mM HEPES and 0.05 mM β-mercaptoethanole.

Depletion of Macrophages/Monocytes

Sterile 6-well plates (cell culture grade) were used to deplete macrophages and monocytes through unspecific adhesion. Each well was filled at maximum with 4 ml media and up to $6 \times 10^6$ peripheral blood mononuclear cells from the immunized rabbit and allowed to bind for 1 h at 37° C. in the incubator. 50% of the cells in the supernatant were used for the panning step; the remaining 50% of cells were kept on ice until the immune fluorescence staining.

Enrichment of B Cells on IL33R Protein 6-well tissue culture plates coated with IL33R protein were seeded with up to $6 \times 10^6$ cells per 4 ml medium and allowed to bind for 1 h at 37° C. in the incubator. After the enrichment step on IL33R protein non-adherent cells were removed by carefully washing the wells 1-2 times with 1×PBS. The remaining sticky cells were detached by trypsin for 10 min at 37° C. in the incubator and then washed twice in media. The cells were kept on ice until the immune fluorescence staining.

Immune Fluorescent Staining and Flow Cytometry

Anti-rabbit IgG FITC used for single cell sorting was from AbD Serotec (STAR121F, Düsseldorf, Germany). For surface staining, cells from the depletion and panning step were incubated with the optimally diluted Anti-rabbit IgG FITC antibody in PBS for 30 min rolling in the cold room at 4° C. in the dark. Following centrifugation, the supernatants were removed by aspiration. The PBMCs were subjected to 2 cycles of centrifugation and washing with ice cold PBS. Finally the PBMCs were resuspended in ice cold PBS and immediately subjected to the FACS analyses. Propidium iodide in a concentration of 5 µg/ml (BD Pharmingen, San Diego, Calif., USA) was added prior to the FACS analyses to discriminate between dead and live cells. A Becton Dickinson FACSAria™ equipped with a computer and the FACSDiva™ software (BD Biosciences, USA) were used to collect and analyse the data.

B Cell Culture

B cell cultures were prepared by a method similar to that described by Zubler, et al., Eur. J. Immunol. 14 (1984) 357-363, Zubler, et al., J. Exp. Med. 160 (1984) 1170-1183. Briefly, single sorted B cells were cultured in 96-well plates with 210 µl/well medium with Pansorbin® Cells (1:20000) (Calbiochem (Merck), Darmstadt, Deutschland), 5% rabbit thymocyte supernatant (charge 20080910, production Irmgard Thorey) and gamma-irradiated EL-4-B5 murine thymoma cells ($2 \times 10^4$/well) for 7 days at 37° C. in an atmosphere of 5% $CO_2$ in the incubator. B cell culture supernatants were removed for screening and the cells harvested immediately for variable region gene recovery or frozen at −80° C. in 100 µl RLT buffer (Qiagen, Hilden, Germany).

Isolation of Ribonucleic Acid (RNA)

The cells from which the RNA had to be isolated were at first pelleted by centrifugation. The cell pellet was lysed by the addition of 100 µl RLT-buffer with 10 µl/ml beta-mercaptoethanol. The cells were resuspended by multiple mixing with a pipette and transferred to a multi well plate. The plate was shortly centrifugated at 200×g and frozen at −20° C. The isolation of the RNA was performed with the NucleoSpin® 96 RNA kit (Macherey & Nagel) according to the manufacturer's instructions.

Reverse Transcription Polymerase Chain Reaction

The reverse transcription was carried out with SuperScript III First-Strand Synthesis SuperMix (Invitrogen) according to the manufacturer's instructions.

Polymerase Chain Reaction

The polymerase chain reaction was carried out with AccuPrime Pfx SuperMix (Invitrogen) according to the manufacturer's instructions. Light chain and heavy chain variable regions were amplified in separate reactions. PCR-primers were used with 25 bp overlaps to target antibody expression vectors. PCR-products were purified by NucleoSpin® 96 Extract II kit (Macherey & Nagel).

Sequencing and SLIC Cloning

The PCR products were sequenced to determine the DNA-sequences of the variable regions of heavy and light chains. The PCR-products were cloned into expression vectors by the so called SLIC-cloning method, which is described by Haun, R. S., et al., in BioTechniques 13 (1992) pp. 515-518 and Li, M. Z., et al., in Nature Methods 4 (2007) pp. 251-256. The plasmids for the antibody expression were linearized by restriction enzyme digestion. The linearized plasmids were purified by preparative agarose electrophoresis and extracted from the gel (Qiaquick Gel Extraction Kit/Qiagen). The purified plasmids were added to a PCR-protocol using overlapping primers (bay 25 bp) for the PCR-product to be cloned. Both the vector and insert were treated with T4 DNA polymerase (Roche Applied Sciences) in the absence of dNTPs to generate overhangs, then vector and insert were incubated with RecA (New England Biolabs) protein and ATP to promote recombination. Products were transformed into E. coli. Plasmid DNAs for light chain and heavy chains were isolated and each couples were combined for transient transfections.

Transient Transfection for Antibody Expression in HEK293 Cells

HEK293 cells (Invitrogen) were grown in F17-media (Gibco) to 1×10e6 cells/ml. 2×10e6 HEK293 cells were transfected with 1 µg HC+LC plasmids suspended in 293-free (Novagen) and OptiMEM® (Gibco). After 7 days incubation supernatants were harvested and analyzed.

Antibodies according to the invention show high quality based on the inhibition of IL33 induced NFkB activation in human UT-7 cells. Preferably the antibodies according to the invention show an IC50 value of 0.05 nM or lower, and more preferably of 0.03 nM or lower. In addition the antibodies according to the invention show valuable properties in the assay combination of an eosinophil assay, mast cell assay, basophil assay (KU812) and $TH_2$ assay. It was found that antibodies which show an inhibition of IL33 induced NFkB activation in human UT-7 cells of an IC50 value of 0.05 nM or lower, and more preferably of 0.03 nM or lower will have especially useful properties in the treatment of rheumatoid arthritis, ulcerative colitis and asthma. Further preferred are antibodies showing $IC_{50}$ values of 5 nM or lower in the eosinophil assay, mast cell assay, Th2 assay, basophil assay (IL-5).

Example 2

Inhibition of IL33 Binding to ST2 (ELISA)

The test was performed on 384 well MaxiSorp™ microtiter plates (Sigma-Aldrich, Nunc. DE, Cat. No. 464718) at RT. After each incubation step plates were washed 3 times with PBST (Phosphate Buffered Saline Tween®-20). At the beginning, plates were coated with 1 µg/ml goat anti-human IgG Fc fragment (Jackson Imm. Res., US, Cat. No. 109-006-170) for at least 2 hours (h). Thereafter the wells were blocked with PBS supplemented with 0.1% Tween®-20 and 2% BSA (Roche Diagnostics GmbH, DE) for 1 h. 60 ng/ml of recombinant human ST2/IL-1R4 Fc chimera (R&D Systems, UK, Cat. No. 523-ST) or recombinant cyno ST2 Fc chimera was captured for 1 h. Dilutions of purified antibodies or supernatants from hybridoma/B-cells in PBS with 0.5% BSA and 0.05% Tween®-20 were incubated with the receptor protein for 1 h. Biotinylated human IL33 (PeproTech, US, Cat No. 500-P261) was added for an additional hour to build up the complex. IL33 was biotinylated with Sulfo-NHS-LC-Biotin (Thermo Scientific Pierce, US, Cat. No. 21327) according to the manufacturer's protocol and purified using Zeba™ Desalt Spin Column (Thermo Scientific Pierce, US, Cat. No. 89889). Binding of the biotinylated IL33 to the complex was detected with 1:4000 diluted streptavidin HRP (Roche Diagnostics GmbH, DE, Cat. No. 11089153001). After 1 h the plates were washed 6 times with PBST and developed with freshly prepared BM blue POD substrate solution (BM blue: 3,3'-5,5'-Tetramethylbenzidine, Roche Diagnostics GmbH, DE, Cat. No. 11484281001) for 12 minutes at RT. Absorbance was measured at 370 nm. The negative control was defined without addition of ST2/IL-1R4 protein and the positive control was defined with all components but without antibody.

Antibody ra170 shows an IC50 value of 0.32 nM for inhibition of binding to human ST2 and 0.13 nM for cynomolgus ST2.

Example 3

Determination of the Affinity of Anti-hST2 Antibodies to Human ST2 ECD (His-Avitag Monomer)

Instrument: BIACORE® T100

Chip: CM4 (GE Healthcare BR-1005-34)

Coupling: amine coupling

Buffer: 10 mM phosphate buffered saline including 0.05% Tween20 (PBST), pH 7.4, 37° C.

For affinity measurements 10 µg/ml goat anti human Fcg antibody (Jackson Imm. Res., US, Cat. No. 115-005-098) has been coupled to the chip surface for capturing the antibodies binding to ST2. Monomeric human ST2 ECD with 6His Avitag™ (Avidity, LLC, US) was added in various concentrations in solution. Association was measured by injection of ST2 ECD for a contact time of 120 sec. (single cycle-kinetic) at 37° C.; dissociation was measured by washing the chip surface with buffer for 1800 sec. at 37° C. For calculation of apparent $K_D$ and other kinetic parameters the Langmuir 1:1 model was used. Results (average of two measurements) are shown in Table 1.

TABLE 1

Average of affinity data measured by SPR (BIACORE T100) in 10 mM PBST at 37° C., pH 7.4

| Antibody | app. $K_D$ (M) | $k_a$ (1/Ms) | $k_d$ (1/s) | $t_{1/2}$ (min) |
|---|---|---|---|---|
| ra170 IgG4 SPLE | $2.7 \times 10^{-12}$ | $4.6 \times 10^6$ | $1.3 \times 10^{-5}$ | 881 |
| ra170 10.12 | $1.1 \times 10^{-09}$ | $4.9 \times 10^6$ | $5.1 \times 10^{-3}$ | 2 |
| ra170 11.12 | $1.4 \times 10^{-10}$ | $3.1 \times 10^6$ | $4.3 \times 10^{-4}$ | 27 |

Example 4

Inhibition of IL33 Induced NFkB Activation in Human UT-7 Cells a) Reagents:

UT-7 cell line (DSMZ # ACC 137)

Culture medium: RPMI 1640 (Gibco #10509-24) supplemented with 2 mM L-glutamine (Gibco #25030), 1.0 mM sodium pyruvate (Gibco #11360-039), 0.1 mM NEAA (Gibco #11140-035), 10% FCS (Gibco #10509-24), 10 units/mL rhGM-CSF (Roche #11115138)

Recombinant Human IL33 (PeproTech #200-33)

PathScan® Phospho-NFkB p65 (Ser536) Sandwich ELISA Antibody Pair (Cell Signaling #7834)

PathScan® Sandwich ELISA Lysis Buffer (Cell Signaling #7018)

rhTNFalpha (Roche Applied Sci #11371843)

b) Procedure:

UT-7 cells were grown in RPMI 1640 supplemented with 2 mM L-glutamine, 1.0 mM sodium pyruvate, 0.1 mM NEAA, 10% FCS and 10 units/mL GM-CSF in a 7% $CO_2$/95% air mixture at 37° C. Cells were passaged when they reached a density of ~1×10$^6$ cells/ml and diluted to a density of 2×10$^5$ cells/ml. Cell were used for the NFkB assay 2d after passaging. To determine the effective concentration for IL33, UT-7 cells were seeded into a 96-well polypropylene cell culture plate (8.0E+05 cells/well in a total volume of 220 µl growth medium) and were stimulated with various concentrations of recombinant human IL33 (0.1-10 ng/ml) for 15 min at 37° C. Then, plates were centrifuged, washed with ice cold PBS and centrifuged again. PBS was removed and 60 µl PathScan® Sandwich ELISA Lysis Buffer were added per well. Cells were incubated with the lysis buffer for 15 min on ice. Lysates were cleared by centrifugation and supernatants were collected. The lysates were stored at −80° C. until determination of NFkB activation using the PathScan® Phospho-NF-kB p65 ELISA. The ELISA was performed according to the instructions of the manufacturer The data demonstrated that stimulation of NFkB activation was optimal at 1 ng/ml IL33. For antibody testing, UT7 cells were seeded into a 96-well polypropylene cell culture plate (8.0E+05 cells/well) and were incubated with different concentrations of antibodies (0.15 ng/ml-300 ng/ml final concentration) in a total volume of 220 µl growth medium. Cells were incubated with the antibodies for 1 h on ice. Subsequently, cells were stimulated with rhIL33 (1 ng/ml final concentration) for 15 min at 37° C. As control, the maximum NFkB activation of UT7 cells was determined by incubation of UT7 cells with TNF-alpha (30 ng/ml) for 15 min at 37° C. Lysate preparation and NFkB analysis was performed as described above. Results are shown in table 2.

TABLE 2

Inhibition of IL33 induced NFkB activation in human UT-7 cells

| Antibody | NFkB IC50 [nM] |
|---|---|
| ra170 (rabbit IgG1) | 0.025 |
| ra170 10.12 | 0.28 |
| ra170 11.12 | 0.04 |
| Mab523[1] | 1.90 |
| AF523 (PAB, goat IgG1)[1] | 0.56 |
| HB12 (mouse IgG1)[1] | 1.43 |
| 2A5[2] | 66.22 |
| FB9[2] | 0.95 |

[1]available from R&D Systems
[2]available from MBL International Corporation, Order numbers: D065-3, D066-3, D067-3 and ABIN130564

Example 5

Binding Site Definition for Clone Ra170

For the definition of the antibody binding sites, human IL33 Receptor ST2 was cloned and expressed. ST2 is composed of 3 domains D1, D2, D3. Thereof a D1D2 variant was generated and residual binding of ra170 was tested. Ra170 binds to ST2 and the truncated variant D1D2.

Binding to the ST2-variant was measured by Surface Plasmon Resonance (SPR) using a BIAcore® T100 instrument (GE Healthcare) at 25° C. The BIAcore® system is well established for the study of molecule interactions. SPR-technology is based on the measurement of the refractive index close to the surface of a gold coated biosensor chip. Changes in the refractive index indicate mass changes on the surface caused by the interaction of immobilized ligand with analyte injected in solution. If molecules bind immobilized ligands on the surface the mass increases, in case of dissociation the mass decreases reflecting the complex dissociation. SPR allows a continuous real-time monitoring of ligand/analyte bindings and thus the determination of association rate constants (ka), dissociation rate constants (kd), and equilibrium constants (KD). Injecting a single concentration value gives a clear statement about the binding abilities of the analyte, but gives also a rough suggestion about the binding values.

Amine coupling of around 8000 resonance units (RU) of a capturing system (capturing ST2-His specific Penta-His, Qiagen, Cat. nr. 34660) was performed on a CM5 chip at pH 5.0 using an amine coupling kit supplied by the GE Healthcare.

For analysis His-tagged ST2-variant was captured by injecting a 300 nM solution for 1 min at a flow of 30 µl/min. Then the antibody to be tested was injected at a concentration of 100 nM for 2 min at a flow of 30 µl/min. The dissociation phase was monitored for up to 1 min and triggered by switching from the sample solution to running buffer. The surface was regenerated by 30 sec. washing with a glycin pH2.0 solution at a flow rate of 30 µl/min.

Bulk refractive index differences were corrected by subtracting the response obtained from a blank-coupled surface. Blank injections are also subtracted (=double referencing).

ST2 variant is bound by antibodies according to the invention comparable to the ST2 wildtype and it is therefore concluded that binding site is located on the D1D2 domain.

Example 6

Determination of the Binding of Anti-IL33R Antibody Towards Different ST2-Variants Binding of an antibody according to the invention to different ST2-variants was measured by Surface Plasmon Resonance (SPR) using a BIAcore® A100 instrument (GE Healthcare) at 37° C. The BIAcore® system is well established for the study of molecule interactions. SPR-technology is based on the measurement of the refractive index close to the surface of a gold coated biosensor chip. Changes in the refractive index indicate mass changes on the surface caused by the interaction of immobilized ligand with analyte injected in solution. If molecules bind immobilized ligands on the surface the mass increases, in case of dissociation the mass decreases reflecting the complex dissociation. SPR allows a continuous real-time monitoring of ligand/analyte bindings and thus the determination of association rate constants (ka), dissociation rate constants (kd), and equilibrium constants (KD).

Amine coupling of around 800 resonance units (RU) of a capturing system (capturing mFcγ-specific anti-mouse Fcγ, Jackson Imm. Res., Cat. nr. JIR115-005-071 and rbFcg-specific anti-rabbit Fcg, Jackson Imm. Res., Cat. nr. JIR111-005-046) was performed on a CM5 chip at pH 5.0 using an amine coupling kit supplied by the GE Healthcare.

For analysis different antibodies were captured by injecting a 10 nM of rabbit antibodies and around 30 nM of mouse antibodies solution for 2 min at a flow of 10 µl/min. Then the His tagged ST2 variants to be tested were injected at a dilution series with a maximal concentration of 150 nM for 2.5 min at a flow of 30 µl/min. The dissociation phase was monitored for up to 10 min and triggered by switching from the sample solution to running buffer. The surface of anti-mouse capture antibodies was regenerated by 60 sec. washing with a glycin pH 1.5 solution followed by 60 sec. washing with a glycine pH2.0 using instrumental protocol. The surface of anti-rabbit capture antibodies was regenerated by two washing steps a 60 sec. with a glycine pH 1.7 solution.

Bulk refractive index differences were corrected by subtracting the response obtained from a blank-coupled surface. Blank injections are also subtracted (=double referencing).

If a ST2 variant is bound by the investigated antibody comparable to ST2 wildtype, the variation does not influence the binding of the antibody to ST2 and it is therefore concluded that binding site is located outside the mutated ST2 region.

If a ST2 variant is not bound by the investigated antibody comparable to ST2 wildtype, the variation influences the binding of the antibody to ST2 and it is therefore concluded that binding site is located within the mutated ST2 region.

Binding properties for antibodies are shown in Table 3. Ra170 binding is influenced by Mut2 and Mut3 indicating that its binding site is overlapping with the mutated sequence stretches. Mab523 binding is influenced by Mu2 and Mut3 but also Mut4 indicating a broader binding region.

TABLE 3

Binding of anti-IL33R antibody towards different ST2-variants

| Antibody | Binding | | | |
|----------|---------|------|------|------|
|          | Mut1    | Mut2 | Mut3 | Mut4 |
| Ra170    | +       | −    | −    | +    |
| MAB523   | +       | −    | −    | −    |

TABLE 4

ST2 Mutants

| Mutant | Replaced ST2 sequence fragment | IL-1R sequence fragment, replacing ST2 sequence fragment |
|--------|-------------------------------|----------------------------------------------------------|
| Mut1   | SEQ ID NO: 13                 | SEQ ID NO: 17                                            |
| Mut2   | SEQ ID NO: 14                 | SEQ ID NO: 18                                            |
| Mut3   | SEQ ID NO: 15                 | SEQ ID NO: 19                                            |
| Mut4   | SEQ ID NO: 16                 | SEQ ID NO: 20                                            |

Example 7

NK-Assay

IL33 amplifies both $T_H1$ and $T_H2$ responses by activating different leukocytes and also NK cells (Smithgall, M. D., et al., Int. Immunol. 20 (2008) 1019-1030). In the following assay, the secretion of IFN-γ by NK cells was induced by co-culture of IL12 and IL33 and its inhibition served as read-out during the characterisation of anti-IL33R antibodies.

After isolation of white blood cells (lymphocytes) from healthy blood, NK cells were purified from PBMC using the negative NK cell isolation kit (Miltenyi, #130-092-657). The average purity was >96%.

Reagents

Human IL-12 (Sigma, #I2276, final concentration [f.c.]=1 ng/ml)

Human IL33 (Peprotech, #200-33, f.c.=10 ng/ml)

IFN-γ CBA flex set (BD, #558269)

NK-cell medium: RPMI 1640 (PAN, # P04-17500), supplemented with 10% FCS (Invitrogen or PAA), 1% sodium pyruvate (Gibco Invitrogen, #11360) and L-Glutamine (Gibco Invitrogen, #25030-024), as well as 0.1% β-Mercaptoethanol (Gibco Invitrogen, #31350-010).

$1 \times 10^5$ NK cells/well were seeded into a 96 well flat bottom plate, optionally pretreated with sample or isotype control antibodies at different concentrations and incubated for one hour at 37° C. NK cells were then stimulated with 10 ng/ml IL33 and 1 ng/ml IL-12 and incubated for 20 hrs. After this, supernatants were harvested, centrifugated and tested for IFN-γ production. For IFN-γ quantification the CBA flex set platform (BD™, using a FACS Canto II) was used. IC50 value was determined to be 0.27 nM for ra170, 1.3 nM for ra170 10.12, 1.8 nM for ra170 11.12, 2.3 nM for PAB AF523 and no inhibition for Mab 523.

Example 8

Eosinophil Viability Assay

To describe the impact of IL33 in prolonging eosinophil survival an assay based on Chow, J. Y., et al., Cellular & Molecular Immunology 7 (2010) 26-34, was established using freshly isolated eosinophils. As the viability of human eosinophils depends on addition of IL33, the pre-incubation with anti-human IL33R [ST2] mAbs at different concentrations inhibited this effect. Granulocytes were isolated from whole blood by Ficoll-Paque™ PLUS gradient centrifugation (GE Healthcare, #17-1440-03). After erythrocyte lysis, the sedimented red cell/granulocyte pellet was taken to purify eosinophils via a negative eosinophil cell isolation kit (Miltenyi Biotec, Bergisch Gladbach, #130-092-010).

Reagents:
- Human IL33 (20 ng/ml)
- Cell Titer Glo®, Luminescent Cell Viability Assay (Promega, #7571)
- Eosinophil cell medium: RPMI 1640 supplemented with FCS, 1% sodium pyruvate, L-glutamine, and 0.1% β-Mercaptoethanol.

$1 \times 10^5$ eosinophils/well were transferred into a 96 well flat bottom plate before medium containing sample antibody was added [5 µg/ml final concentration] and incubated for one hour at 37° C. Then, IL33 was added at a final concentration of 20 ng/ml and eosinophils were incubated at 37° C. in a humidified incubator. After 40 hrs, eosinophil viability was determined. For ra170 an $IC_{50}$ value of 1.3 nM was found.

Example 9

Primary Mast Cell Assay

Mast cells are central in the development and maintenance of allergic reactions by amplification of both innate and adaptive immune responses. Mast cells are localized in tissues and not in circulating blood. Thus, to obtain human mast cells from blood, $CD34^+$ hematopoietic progenitor cells were differentiated into mast cells in the presence of human stem cell factor (SCF), IL-3 and IL-6 within 5-6 weeks. The following protocol is based on the publication by Saito, H., et al., Nature Protocols 1 (2006), 2178-2183.

After isolation of white blood cells (see example 10), CD34+ hematopoietic progenitor cells were purified from PBMC using the CD34 MicroBead kit (Miltenyi Biotec, #130-046-702). The average yield was $1-2 \times 10^5$ total cells per donor; usually 50% $CD34^+ CD117^+$ cells were obtained.

Reagents and Differentiation Protocol:
- Methocult® (Stem Cell Tech., # H4236)
- Insulin-transferrin-selenium supplement (Invitrogen, #51300-044)
- BSA, bovine serum albumin
- Human SCF
- Human IL3 and IL6
- Basic Mast Cell medium (bMC): IMDM (Iscove's Modified Dulbecco's Medium), supplemented with 0.1% β-Mercaptoethanol and 1% Penicillin/Streptomycin.

After purification, $1.5 \times 10^5$ purified CD34+ cells were resuspended in bMC medium, supplemented with IL-3, IL-6 and SCF, BSA, Methocult®, and Insulin-transferrin-selenium supplement and seeded into 10-12 wells of a 24 well plate and cultured for 5-6 weeks.

Functional Mast Cell Assay

After the expansion and differentiation phase mast cells were used in a functional assay analyzing the antagonistic impact of anti-IL33R antibodies.

Reagents and Medium
- 20 ng/ml human IL33
- Human IL-5
- Human IL-13
- Basic Mast Cell medium.

$10^5$ mast cells/well were seeded into a flat bottom 96 well plate. First, mast cells were pre-treated with sample or isotype control antibodies for one hour at 37° C. For $IC_{50}$ determination antibodies were used at different concentrations, usually starting with a f.c. of 5 µg/ml and diluted in 1:3 steps. 20 ng/ml IL33 was then added and cells were incubated for approximately 40 to 48 hrs at 37° C. before (inhibition of) $T_H2$ cytokine levels were quantified. After the indicated incubation time, cell suspensions were transferred into a V-bottom plate and sedimented (400×g, 10 min at RT). The supernatant was then used to determine cytokine levels (IL-5 and IL-13). For ra170 $IC_{50}$ values up to 0.4 nM (IL-13) and 0.2 (IL-5) were found.

Example 10

Human Th2 Assay

Peripheral blood mononuclear cells (PBMC) were isolated from healthy volunteers by a Ficoll Hypaque density gradient. After washing the cells with PBS pH 7.2 with 2 mM EDTA, cells were washed once with PBS pH 7.2 with 0.5% BSA and 2 mM EDTA. Naive CD4+ T cells were isolated from PBMC using CD4+ T cell isolation kit II (Miltenyi Biotec) and magnetic separation. The enriched T cells were washed 3 times using completed RPMI 1640 (supplemented with 10% FCS, 2-mercaptoethanol, L-glutamine, sodium pyruvate, non-essential amino acids, and Penicillin/Streptomycin), resuspended and plated at $0.5 \times 10^6$ cells/ml in 6 well flat bottom plates, with 1:1 ratio of Dynabeads T-Activator CD3/CD28 (Invitrogen), 10 ng/ml of IL-2, 10 ng/ml of IL-4, 5 µg/ml of anti-IL-12 (R&D System), and 5 µg/ml of anti-IFNγ (R&D System), and incubated for 4 days at 37° C. Cells were split, then kept in the same culture condition for another 4 days. Cells were washed with completed RPMI two times and then rested at $1 \times 10^6$ cells/ml in completed RPMI with 2 ng/ml of IL2 for 3 days. One day before the assay, High-binding 96-wells flat-bottom plates (Costar) were coated with 5 µg/ml of soluble anti-CD3e (BD Bioscience). On the assay day, cells were washed with complete RPMI twice, and rest for another 4 hours without IL-2. Plates were washed with PBS three times. $1 \times 10^5$ cells/well were plated in complete RPMI, supplemented with 1 µg/ml of anti-CD28 (BD Bioscience). Cells were subsequently treated with serial dilution of anti-ST2 Ab or isotype control Ab (0-10 µg/ml) for 30 min, then restimulated with 10 ng/ml of IL33 (Peprotech), in a total volume of 200 µl, then cultured at 37° C. under 5% $CO_2$ for 64 hours. Supernatants were collected for IL-5/IL-13 ELISA (R&D Systems). For ra170 IC50 value was determined to be 2.77±2.58 nM (Mean±SD, n=6) for IL-5, and 1.10±1.05 (Mean±SD, n=5) for IL-13.

Example 11

Cynomolgus NK Cell Assay

Peripheral blood mononuclear cells (PBMC) were isolated from cynomolgus by a Ficoll Hypaque density gradient. After washing the cells with PBS pH 7.2 with 2 mM EDTA, cells were washed once with PBS pH 7.2 with 0.5% BSA and 2 mM EDTA. NK cells were isolated from PBMC following non-human primate CD16 Microbeads positive selection after monocytes depletion by non-human primate CD56 Microbeads (Miltenyi Biotec) and magnetic separation by AutoMACS™ separator. The enriched NK cells were washed three times using completed RPMI 1640 (supplemented with 10% FCS, 2-mercaptoethanol, L-glutamine, sodium pyruvate, non-essential amino acids, and Penicillin/Streptomycin), resuspended and plated at $2.5 \times 10^4$ cells/well in 96 well round bottom plates in complete RPMI. Cells were subsequently treated with serial dilution of anti-ST2 Ab or isotype control Ab (0-10 µg/ml) for 30 min, restimulated with 20 ng/ml of human IL33 plus 10 ng/ml of recombinant cynomolgus IL-12 in a total volume of 200 µl, then cultured at 37° C. under 5% $CO_2$ for 24 hours. Supernatants were collected for cynomolgus IFNγ ELISA (MabTech). IC50 value was determined to be 0.109±0.073 nM (Mean±SD, n=3) for ra170.

Example 12

Basophil Cell Line (KU812) Assay

The human basophil cell line KU812 (ATCC CRL 2099) was cultured in RPMI 1640 medium with 10% FBS and Penicillin/Streptomycin. Cells were split twice a week with cell density not more than 0.5 million cells/ml. Quality controls were routinely performed by FACS analysis of cells surface expression of c-kit and FceRI. On the assay day, KU812 cells (0.2 million cells/well) were seeded in 96 well round bottom culture plates with fresh complete medium. Cells were treated with serial dilution of antibodies or control isotypes for 1 hour at 37° C. After treatment, cells were stimulated with 10 ng/ml IL33 (Peprotech) overnight at 37° C. incubator. Cells were spun down and supernatants were collected for cytokine analysis. Cytokines (IL-5, IL-13, and GM-CSF) were analyzed following the MSD manufactory procedure. For ra170 IC50 values from three independent experiments were determined to be 3.49±3.43 nM (Mean±SD, IL-13), 1.48±0.75 nM (Mean±SD, IL-5), and 1.31±1.22 nM (Mean±SD, GM-CSF). For ra170 IC90 values were determined to be 7.51±0.99 nM (Mean±SD, IL-13), 4.60±1.65 nM (Mean±SD, IL-5), and 9.10±4.74 nM (Mean±SD, GM-CSF).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. An anti-human IL33R antibody, wherein said antibody has a heavy chain variable domain comprising a CDR3 region of SEQ ID NO:24, a CDR2 region of SEQ ID NO:23 and a CDR1 region of SEQ ID NO:22 and a light chain variable domain comprising a CDR3 region of SEQ ID NO:33, a CDR2 region of SEQ ID NO:32 and a CDR1 region of SEQ ID NO:31.

2. The antibody according to claim 1, wherein the heavy chain variable domain comprises SEQ ID NO:21.

3. The antibody according to claim 2, wherein the heavy chain variable domain comprises SEQ ID NO:21 and the light chain variable domain comprises SEQ ID NO:30.

4. The antibody according to claim 1, which is a chimeric antibody, a humanized antibody or a T cell epitope-depleted antibody.

5. An anti-human IL33R antibody having a human IgG1 or IgG4 isotype but modified in the hinge region at one or more amino acid position between 216-240, and/or in the second inter-domain region at one or more amino acid position between 327-331 between $C_H2$ and $C_H3$, wherein said antibody is selected from:
   a) An anti-human IL33R antibody comprising a heavy chain variable domain comprising a CDR3 region of SEQ ID NO:24, a CDR2 region of SEQ ID NO:23 and a CDR1 region of SEQ ID NO:22 and a light chain variable domain comprising a CDR3 region of SEQ ID NO:33, a CDR2 region of SEQ ID NO:32 and a CDR1 region of SEQ ID NO:31;
   b) An anti-human IL33R antibody, wherein the heavy chain variable domain comprises SEQ ID NO:21 and the light chain variable domain comprises SEQ ID NO:30; or
   c) An anti-human IL33R antibody according to a) or b), which is a chimeric antibody, a humanized antibody or a T cell epitope-depleted antibody.

6. An anti-human IL33R antibody according to claim 5, wherein said hinge region is modified by replacing the amino acid at position 234 and the amino acid at position 235 with alanine.

7. An anti-human IL33R antibody according to claim 5, wherein said hinge region is modified by replacing the amino acid at position 235 and the amino acid at position 228 with glutamic acid and proline, respectively.

8. A pharmaceutical composition comprising an anti-human IL33R antibody, wherein said antibody is selected from:
   a) An anti-human IL33R antibody comprising a heavy chain variable domain comprising a CDR3 region of SEQ ID NO:24, a CDR2 region of SEQ ID NO:23 and a CDR1 region of SEQ ID NO:22 and a light chain variable domain comprising a CDR3 region of SEQ ID NO:33, a CDR2 region of SEQ ID NO:32 and a CDR1 region of SEQ ID NO:31;
   b) An anti-human IL33R antibody, wherein the heavy chain variable domain comprises SEQ ID NO:21 and the light chain variable domain comprises SEQ ID NO:30; or
   c) An anti-human IL33R antibody according to a) or b) having a human IgG1 or IgG4 isotype but modified in the hinge region at one or more amino acid position between 216-240, and/or in the second inter-domain region at one or more amino acid position between 327-331 between $C_H2$ and $C_H3$;
   d) An anti-human IL33R antibody according to c), wherein said hinge region is modified by replacing the amino acid at position 234 and the amino acid at position 235 with alanine; or
   e) An anti-human IL33R antibody according to c), wherein said hinge region is modified by replacing the amino acid at position 235 and the amino acid at position 228 with glutamic acid and proline, respectively;
   and a pharmaceutically acceptable carrier.

9. A pharmaceutical composition according to claim 8, wherein the antibody binds to the same IL33R epitope to which the antibody according to claim 3 binds.

10. A nucleic acid encoding a heavy chain of an antibody binding to IL33R, wherein said antibody comprises a CDR3 region of SEQ ID NO:24, a CDR2 region of SEQ ID NO:23 and a CDR1 region of SEQ ID NO:22 and a light chain variable domain comprises a CDR3 region of SEQ ID NO:33, a CDR2 region of SEQ ID NO:32 and a CDR1 region of SEQ ID NO:31.

11. An expression vector comprising a nucleic acid encoding an anti-human IL33R antibody or antigen binding fragment thereof selected from:
   a) An anti-human IL33R antibody comprising a heavy chain variable domain comprising a CDR3 region of SEQ ID NO:24, a CDR2 region of SEQ ID NO:23 and a CDR1 region of SEQ ID NO:22 and a light chain variable domain comprising a CDR3 region of SEQ ID NO:33, a CDR2 region of SEQ ID NO:32 and a CDR1 region of SEQ ID NO:31;
   b) An anti-human IL33R antibody, wherein the heavy chain variable domain comprises SEQ ID NO:21 and the light chain variable domain comprises SEQ ID NO:30;
   c) An anti-human IL33R antibody according to a) or b) having a human IgG1 or IgG4 isotype but modified in the hinge region at one or more amino acid position between 216-240, and/or in the second inter-domain region at one or more amino acid position between 327-331 between CH2 and CH3;
   d) An anti-human IL33R antibody according to c), wherein said hinge region is modified by replacing the amino acid at position 234 and the amino acid at position 235 with alanine; or
   e) An anti-human IL33R antibody according to c), wherein said hinge region is modified by replacing the amino acid at position 235 and the amino acid at position 228 with glutamic acid and proline, respectively.

12. The vector according to claim 11, wherein the vector is capable of expressing the anti-human IL33R antibody or antigen binding fragment thereof in a host cell.

13. A host cell comprising a vector according to claim 11.

14. The host cell of claim 13 wherein the host cell is a prokaryotic cell.

15. The host cell of claim 13 wherein the host cell is a eukaryotic cell.

16. A method for producing a recombinant anti-human IL33R antibody or antigen binding fragment thereof comprising a heavy chain variable domain comprising a CDR3 region of SEQ ID NO:24, a CDR2 region of SEQ ID NO:23 and a CDR1 region of SEQ ID NO:22 and a light chain variable domain comprising a CDR3 region of SEQ ID NO:33, a CDR2 region of SEQ ID NO:32 and a CDR1 region of SEQ ID NO:31, said method comprising culturing a host cell according to claim 13 and recovering said antibody from said cell or the cell culture supernatant.

* * * * *